(12) United States Patent
Ueda et al.

(10) Patent No.: US 10,524,704 B2
(45) Date of Patent: Jan. 7, 2020

(54) PULSE PHOTOMETER AND METHOD FOR CALCULATING CONCENTRATION OF LIGHT ABSORBER IN BLOOD

(71) Applicant: NIHON KOHDEN CORPORATION, Tokyo (JP)

(72) Inventors: Yoshinori Ueda, Tokyo (JP); Teiji Ukawa, Tokyo (JP); Kazumasa Ito, Tokyo (JP); Hideki Fujisaki, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 549 days.

(21) Appl. No.: 15/059,564

(22) Filed: Mar. 3, 2016

(65) Prior Publication Data

US 2016/0256089 A1 Sep. 8, 2016

(30) Foreign Application Priority Data

Mar. 4, 2015 (JP) ................................ 2015-042600
Jan. 20, 2016 (JP) ................................ 2016-008856

(51) Int. Cl.
*A61B 5/1455* (2006.01)
*A61B 5/00* (2006.01)

(52) U.S. Cl.
CPC ............ *A61B 5/14551* (2013.01); *A61B 5/72* (2013.01)

(58) Field of Classification Search
CPC ..... A61B 5/14551; A61B 5/72; A61B 5/1455; A61B 5/14552; A61B 5/14532
See application file for complete search history.

(56) References Cited

U.S. PATENT DOCUMENTS

| 5,782,756 | A | 7/1998 | Mannheimer |
| 6,453,184 | B1 | 9/2002 | Hyogo et al. |
| 2004/0267140 | A1 | 12/2004 | Ito et al. |

(Continued)

FOREIGN PATENT DOCUMENTS

| DE | 10 2004 005 086 A1 | 8/2004 |
| JP | 2001-078990 A | 3/2001 |
| JP | 4196209 B2 | 12/2008 |
| JP | 2011-206285 A | 10/2011 |

OTHER PUBLICATIONS

Nogawa et al. New Hybrid Reflectance Optical Pulse Oximetry Sensor for Lower Oxygen Saturation Measurement and for Broader Clinical Application, Proc. SPIE 2976, Jun. 16, 1997.*

(Continued)

*Primary Examiner* — Eric F Winakur
*Assistant Examiner* — Chu Chuan Liu
(74) *Attorney, Agent, or Firm* — Pearne & Gordon LLP

(57) ABSTRACT

A pulse photometer includes: a first variation acquirer acquiring a first variation corresponding to a light attenuation variation of a first light beam due to pulsation of blood in a subject, based on a first intensity signal corresponding to an intensity of the first light beam that is transmitted through or reflected from a body of the subject, and that has a first wavelength; a second variation acquirer acquiring a second variation; and a concentration calculator calculating a blood light absorber concentration, based on the first and second variations, the second variation containing a first offset which is based on an inverse of the light attenuation variation of the first light beam.

11 Claims, 4 Drawing Sheets

(56) References Cited

U.S. PATENT DOCUMENTS

| | | | | |
|---|---|---|---|---|
| 2008/0221463 A1* | 9/2008 | Baker | ............... | A61B 5/02416 |
| | | | | 600/500 |
| 2009/0318787 A1* | 12/2009 | Aoyagi | ............... | A61B 5/1455 |
| | | | | 600/323 |
| 2010/0160794 A1* | 6/2010 | Banet | ............... | A61B 5/02125 |
| | | | | 600/485 |
| 2010/0324384 A1* | 12/2010 | Moon | .................. | A61B 5/1118 |
| | | | | 600/323 |

OTHER PUBLICATIONS

Suzaki et al., 'Noninvasive measurement of total hemoglobin and hemoglobin derivatives using multiwavelength pulse spectrophotometry', IEEE, Aug. 30, 2006.*

Takatani et al., Experimental and Clinical Evaluation of a Noninvasive Reflectance Pulse Oximeter Sensor, J. Clinical Monitoring, vol. 8, No. 4, Oct. 1992.*

Mendelson, "Pulse Oximetry", Wiley Encyclopedia of Biomedical Engineering, 2006, pp. 1-18.*

Extended European Search Report issued in Application No. EP 16 15 8445 dated Jul. 20, 2016.

Setsuo Takatani et al., "Experimental and Clinical Evaluation of a Noninvasive Reflectance Pulse Oximeter Sensor", Journal of Clinical Monitoring, vol. 8, No. 4, pp. 257-266, Oct. 1992.

Japanese Office action issued in Japanese Patent Application No. 2016-008856 dated Aug. 20, 2019.

\* cited by examiner

PULSE PHOTOMETER AND METHOD FOR CALCULATING CONCENTRATION OF LIGHT ABSORBER IN BLOOD

CROSS-REFERENCE TO RELATED APPLICATION(S)

This application is based upon and claims the benefit of priority from prior Japanese patent applications No. 2015-042600, filed on Mar. 4, 2015, and No. 2016-008856, filed on Jan. 20, 2016, the entire contents of which are incorporated herein by reference.

BACKGROUND

The presently disclosed subject matter relates to a pulse photometer for calculating the concentration of a light absorption material in blood of a subject (hereinafter, the concentration is often referred to as "blood light absorber concentration"), and a method for calculating the blood light absorber concentration by using the pulse photometer.

A pulse photometer is an apparatus which measures the blood light absorber concentration of the subject. Specifically, the living tissue of the subject is irradiated with light beams at a plurality of wavelengths which have different ratios of the blood light absorbances depending on the blood light absorber concentration. The intensities of the light beams at the wavelengths transmitted through or reflected from the living tissue are detected. The intensities at the wavelengths are changed in accordance with the pulsation of the blood in the subject. Therefore, temporal changes of the intensities at the wavelengths due to the pulsation are acquired in the form of a pulse wave signal. The amplitudes of pulse wave signals with respect to waveforms correspond to light attenuation variations with respect to the waveforms, respectively. The blood light absorber concentration calculated based on a ratio of light attenuation variations with respect to waveforms (for example, see Japanese Patent No. 4,196,209).

As an example of the blood light absorber concentration, known is the arterial oxygen saturation (hereinafter, referred to as the SaO2) which is used as an index of oxygenation of blood. In order to obtain the value of the SaO2, an invasive measurement must be performed. Therefore, the transcutaneous arterial oxygen saturation (hereinafter, referred to as the SpO2) which can be non-invasively calculated is widely used as the index. The SpO2 is measured by a pulse oximeter which is an example of a pulse photometer.

Ideally, the value of the calculated SpO2 is equal to that of the actual SaO2. However, it is known that the values are different from each other under certain conditions. In the case where the pulse wave signal has a low amplitude, particularly, the value of the SpO2 tends to be calculated to be higher than that of the actual SaO2. In this case, a situation where, even when the value of the SpO2 indicates the normal condition of the subject, the subject actually suffers hypoxemia is possibly caused.

SUMMARY

The presently disclosed subject matter may provide an apparatus and a method to improve the accuracy of a blood light absorber concentration which is non-invasively calculated.

There may be provided a pulse photometer comprising: a first variation acquirer which is configured to acquire a first variation corresponding to a light attenuation variation of a first light beam due to pulsation of blood in a subject, based on a first intensity signal corresponding to an intensity of the first light beam that is transmitted through or reflected from a body of the subject, and that has a first wavelength; a second variation acquirer which is configured to acquire a second variation corresponding to a light attenuation variation of a second light beam due to the pulsation of the blood in the subject, based on a second intensity signal corresponding to an intensity of the second light beam that is transmitted through or reflected from the body of the subject, and that has a second wavelength; and a concentration calculator which is configured to calculate a blood light absorber concentration, based on the first variation and the second variation, the second variation containing a first offset which is based on an inverse of the light attenuation variation of the first light beam.

DETAILED DESCRIPTION OF EXEMPLARY EMBODIMENTS

Figure 1:
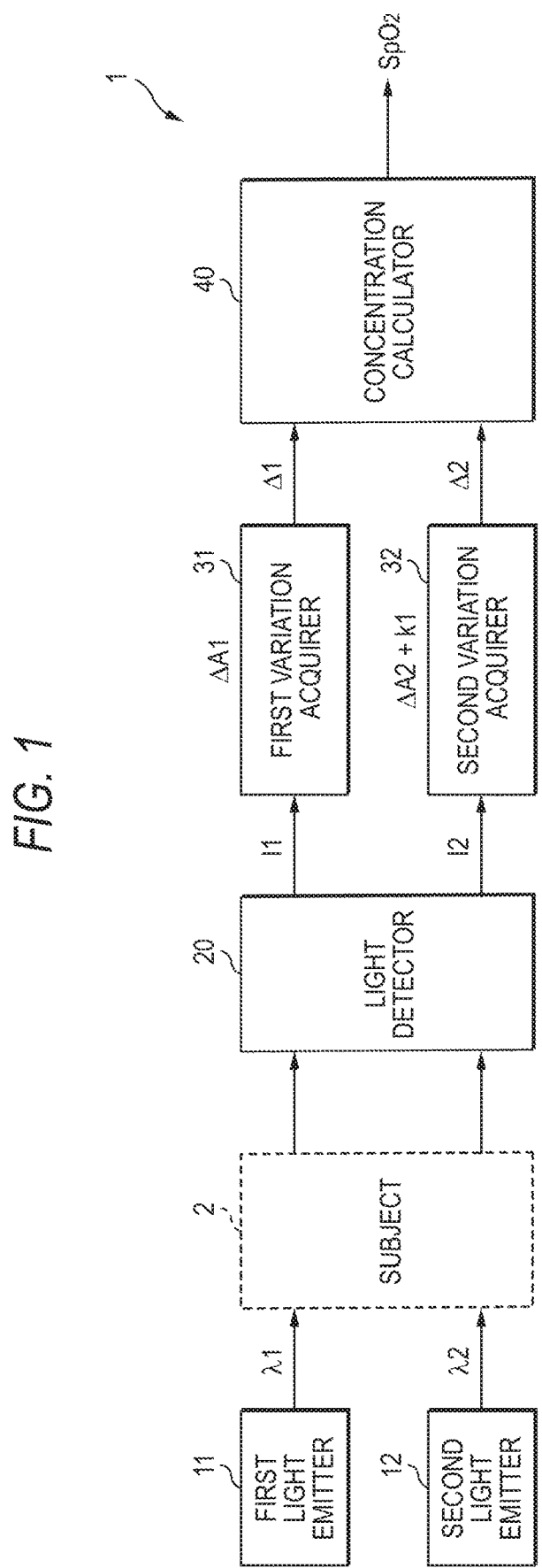
FIG. 1 is a block diagram illustrating the functional configuration of a pulse oximeter of a first embodiment.

Hereinafter, embodiments will be described in detail with reference to the accompanying drawings. FIG. 1 is a block diagram illustrating the functional configuration of a pulse oximeter 1 (an example of the pulse photometer) of a first embodiment. The pulse oximeter 1 is an apparatus which measures the SpO2 of a subject 2. The SpO2 indicates a ratio (an example of the blood light absorber concentration) of oxyhemoglobin (an example of the blood light absorber) to the amount of hemoglobin capable of carrying oxygen.

The pulse oximeter 1 can include a first light emitter 11. The first light emitter 11 is configured so as to emit a first light beam having a first wavelength $\lambda 1$. Examples of the first wavelength $\lambda 1$ are 880 nm and 940 nm (examples of the infrared light beam). For example, the first light emitter 11 is a semiconductor light emitting device which can emit the first light beam. Examples of the semiconductor light emitting device are a light emitting diode (LED), a laser diode, and an organic electroluminescence.

The pulse oximeter 1 can include a second light emitter 12. The second light emitter 12 is configured so as to emit a second light beam having a second wavelength $\lambda 2$. Examples of the second wavelength $\lambda 2$ are 630 nm and 660 nm (examples of the red light beam). For example, the second light emitter 12 is a semiconductor light emitting device which can emit the second light beam. Examples of the semiconductor light emitting device are a light emitting diode (LED), a laser diode, and an organic electroluminescence.

The pulse oximeter 1 can include a light detector 20. The light detector 20 is configured so as to output a first intensity signal I1 in accordance with the intensity of the first light beam transmitted through or reflected from the body of the subject 2. Moreover, the light detector 20 is configured so as to output a second intensity signal I2 in accordance with the intensity of the second light beam transmitted through or reflected from the body of the subject 2. For example, the light detector 20 is an optical sensor having a sensitivity to, for example, the first wavelength λ1 and the second wavelength λ2. Examples of the optical sensor are a photodiode, a phototransistor, and a photoresistor.

The pulse oximeter 1 can include a first variation acquirer 31. The first variation acquirer 31 is configured so as to acquire a light attenuation variation $\Delta A1$ of the first light beam due to the blood pulsation of the subject 2 based on a temporal change of the first intensity signal I1 output from the light detector 20. The light attenuation variation $\Delta A1$ of the first light beam is expressed by the following expression:

$$\Delta A1 = \ln[I1/(I1-\Delta I1)] \approx \Delta I1/I1 \tag{1}$$

where $\Delta I1$ indicates the variation of the first intensity signal I1 due to the blood pulsation of the subject 2.

The pulse oximeter 1 can include a second variation acquirer 32. The second variation acquirer 32 is configured so as to acquire a light attenuation variation $\Delta A2$ of the second light beam due to the blood pulsation of the subject 2 based on a temporal change of the second intensity signal I2 output from the light detector 20. The light attenuation variation $\Delta A2$ of the second light beam is expressed by the following expression:

$$\Delta A2 = \ln[I2/(I2-\Delta I2)] \approx \Delta I2/I2 \tag{2}$$

where $\Delta I2$ indicates the variation of the second intensity signal I2 due to the blood pulsation of the subject 2.

As described above, in the case where the pulse wave signal has a low amplitude, particularly, the value of the SpO2 acquired by the pulse oximeter tends to be higher than that of the arterial oxygen saturation (hereinafter, referred to as the SaO2) which is invasively acquired. The inventors have focused on the light attenuation variation $\Delta A1$ of the first light beam corresponding to the amplitude of the pulse wave signal, and investigated a relationship between the variation and the difference between the value of the SpO2 and that of the SaO2.

Figure 2:
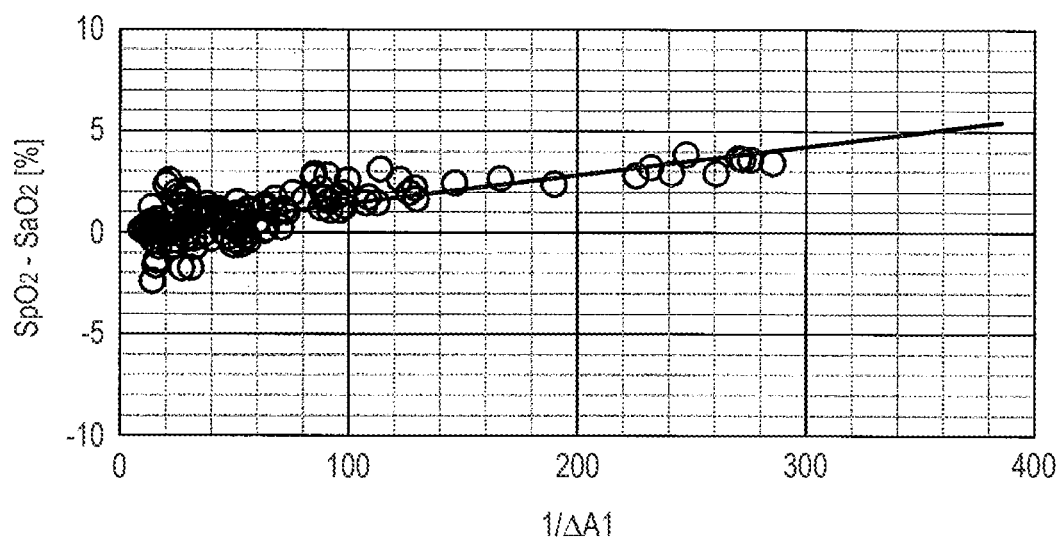
FIGS. 2(A) and 2(B) are views illustrating the operation of the pulse oximeter of FIG. 1.
Figure 2:
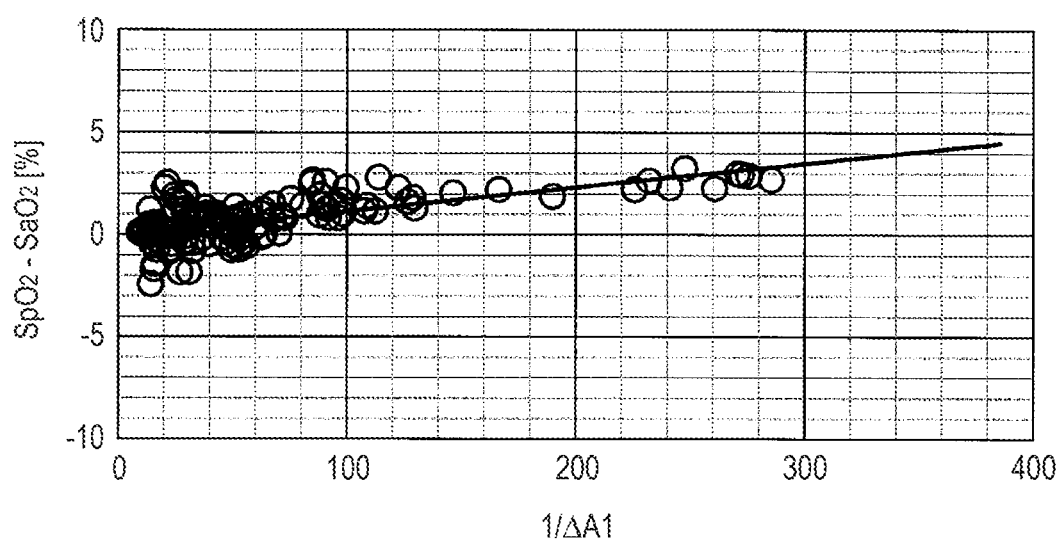

FIG. 2(A) illustrates results of the investigation. The abscissa represents the inverse of the light attenuation variation $\Delta A1$ of the first light beam. Therefore, the figure illustrates a situation where the larger the value, the lower the amplitude of the pulse wave signal. The ordinate represents the difference between the value of the SpO2 and that of the SaO2. Namely, the ordinate indicates the bias contained in the value of the acquired SpO2. The inventors have found that the inverse of the light attenuation variation $\Delta A1$ of the first light beam and the bias contained in the value of the acquired SpO2 are in proportional relationships. That is, the following expression is obtained:

$$SpO2-SaO2 = -k1/\Delta A1 \tag{3}$$

where k1 is a proportional constant.

The value of the SaO2 can be regarded as a reference value for the SpO2 acquired by the pulse oximeter. From Expression (3), the reference value can be expressed by the following expression:

$$SaO2 = SpO2 + (k1/\Delta A1) \tag{4}$$

Namely, the right side of Expression (3) can be regarded as an offset necessary for obtaining the accurate value of the SpO2. According to Expression (4), it is seen that the reference value is obtained by adding the offset to the value of the SpO2 acquired by the pulse oximeter.

On the other hand, the SpO2 is a function of a light attenuation variation ratio $\Phi 21 (=\Delta A2/\Delta A1)$ which is a ratio of the light attenuation variation $\Delta A2$ of the second light beam to the light attenuation variation $\Delta A1$ of the first light beam. From Expression (4), therefore, the following expression is obtained:

$$\begin{aligned} SaO2 &\propto \Phi 21 + (k1/\Delta A1) \\ &\propto (\Delta A2/\Delta A1) + (k1/\Delta A1) \\ &\propto (\Delta A2 + k1)/\Delta A1 \end{aligned} \tag{5}$$

Namely, it is seen that the value of the SpO2 acquired by the pulse oximeter can approach that of the SaO2 by adding an offset corresponding to the proportional constant k1 which is obtained from the relationships shown in FIG. 2(A), to the light attenuation variation $\Delta A2$ of the second light beam.

The first variation acquirer 31 is configured so as to acquire a first variation $\Delta 1$ corresponding to the light attenuation variation $\Delta A1$ of the first light beam. The first variation $\Delta 1$ is substantially identical to the light attenuation variation $\Delta A1$ of the first light beam.

The second variation acquirer 32 is configured so as to acquire a second variation $\Delta 2$ corresponding to the light attenuation variation $\Delta A2$ of the second light beam. The second variation $\Delta 2$ is set as the following expression based on the above-described finding:

$$\Delta 2 = \Delta A2 + k1 \tag{6}$$

In the expression, k1 is regarded as the first offset based on the inverse of the light attenuation variation $\Delta A1$ of the first light beam. That is, the second variation $\Delta 2$ contains the first offset k1.

The pulse oximeter 1 can include a concentration calculator 40. The concentration calculator 40 is configured so as to calculate the SpO2 of the subject 2 based on the first variation $\Delta 1$ acquired by the first variation acquirer 31, and the second variation $\Delta 2$ acquired by the second variation acquirer 32. Specifically, the concentration calculator is configured so as to calculate the SpO2 based on Expression (5).

Similarly with FIG. 2(A), FIG. 2(B) illustrates the difference between the value of the SpO2 which is calculated by the pulse oximeter 1 including the concentration calculator 40, and that of the SaO2. It is seen that, although the difference between the values is not eliminated, the bias in a region where the pulse wave amplitude is low (region where the inverse of the light attenuation variation $\Delta A1$ of the first light beam is large) is reduced as compared with the example in which the first offset k1 is not used. According to the configuration, therefore, it is possible to improve the accuracy of the SpO2 which is non-invasively calculated.

The value of the first offset k1 may be adequately determined. In the embodiment, the value of the first offset k1 is previously statistically determined based on a plurality of difference values between the SpO2 and the SaO2 which are acquired from a plurality of subjects. Specifically, a statistical process such as the least squares method is applied to a plurality of measurement results such as shown in FIG. 2(A), and the first offset k1 by which the difference between the SpO2 and the SaO2 can be reduced is determined.

According to the configuration, the second variation acquirer 32 operates based on the first offset k1 which is a constant that is statistically determined. Therefore, the reliability of the first offset k1 can be improved, and furthermore the processing load of the second variation acquirer 32 can be reduced. Consequently, the accuracy of the SpO2 which is non-invasively calculated can be easily improved.

In the embodiment, an infrared light beam is used as the first light beam, and a red light beam is used as the second light beam. Alternatively, a red light beam may be used as the first light beam, and an infrared light beam may be used as the second light beam.

The embodiment is configured so that the common light detector 20 detects the first light beam emitted from the first light emitter 11, and the second light beam emitted from the second light emitter 12. Alternatively, a configuration may be employed where a light detector for detecting the first light beam, and that for detecting the second light beam are arranged independently from each other.

Figure 3:
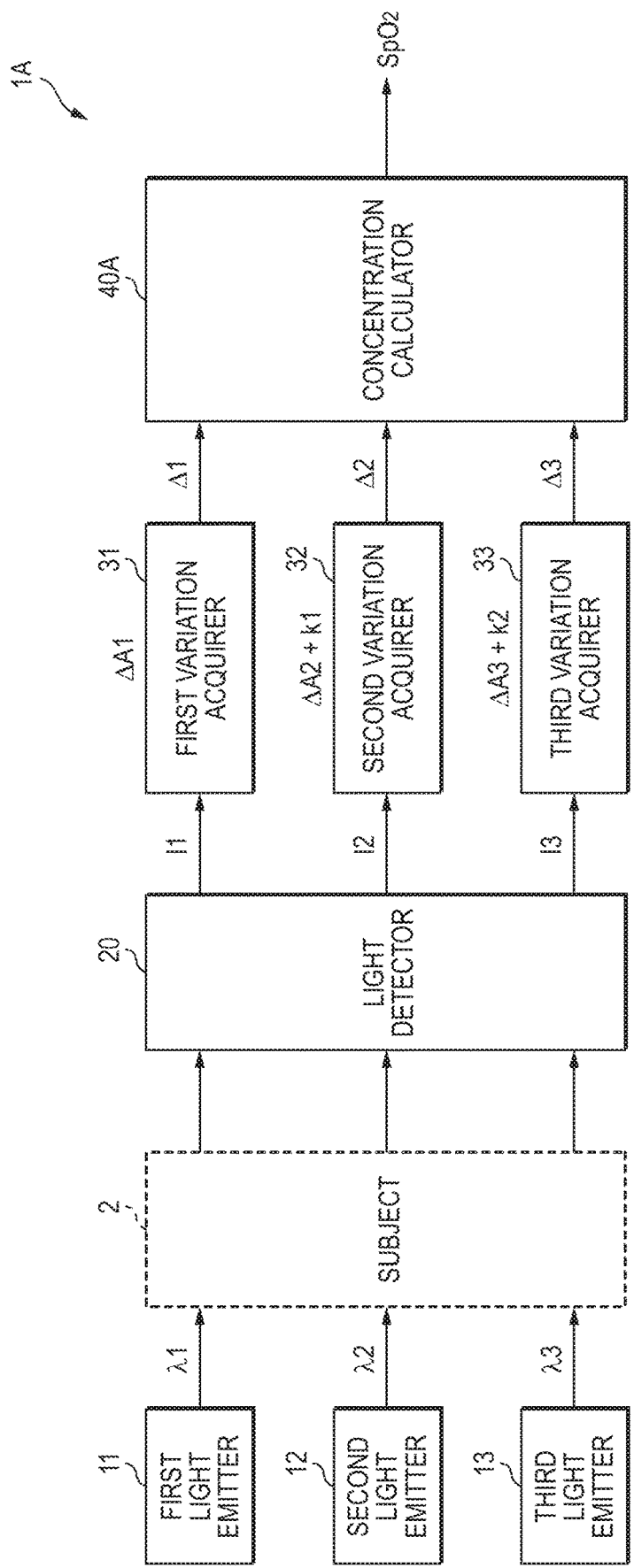
FIG. 3 is a block diagram illustrating the functional configuration of a pulse oximeter of a second embodiment.

FIG. 3 is a diagram illustrating the functional configuration of a pulse oximeter 1A of a second embodiment. Portions which are identical or substantially identical with those of the pulse oximeter 1 of the first embodiment are denoted by the same reference numerals, and duplicated descriptions are omitted.

The pulse oximeter 1A can include a third light emitter 13. The third light emitter 13 is configured so as to emit a third light beam having a third wavelength $\lambda 3$. Examples of the third wavelength $\lambda 3$ are 700 nm (an example of the red light beam) 730 nm (an example of the red light beam), and 805 nm (an example of the infrared light beam). For example, the third light emitter 13 is a semiconductor light emitting device which can emit the third light beam. Examples of the semiconductor light emitting device are a light emitting diode (LED), a laser diode, and an organic electroluminescence.

The light detector 20 is configured so as to output a third intensity signal I3 in accordance with the intensity of the third light beam transmitted through or reflected from the body of the subject 2.

The pulse oximeter 1A can include a third variation acquirer 33. The third variation acquirer 33 is configured so as to acquire a light attenuation variation $\Delta A3$ of the third light beam due to the blood pulsation of the subject 2 based on a temporal change of the third intensity signal I3 output from the light detector 20. The light attenuation variation $\Delta A3$ of the third light beam is expressed by the following expression:

$$\Delta A3 = \ln[I3/(I3-\Delta I3)] \approx \Delta I3/I3 \quad (7)$$

where $\Delta I3$ indicates the variation of the third intensity signal I3 due to the blood pulsation of the subject 2.

Figure 4:
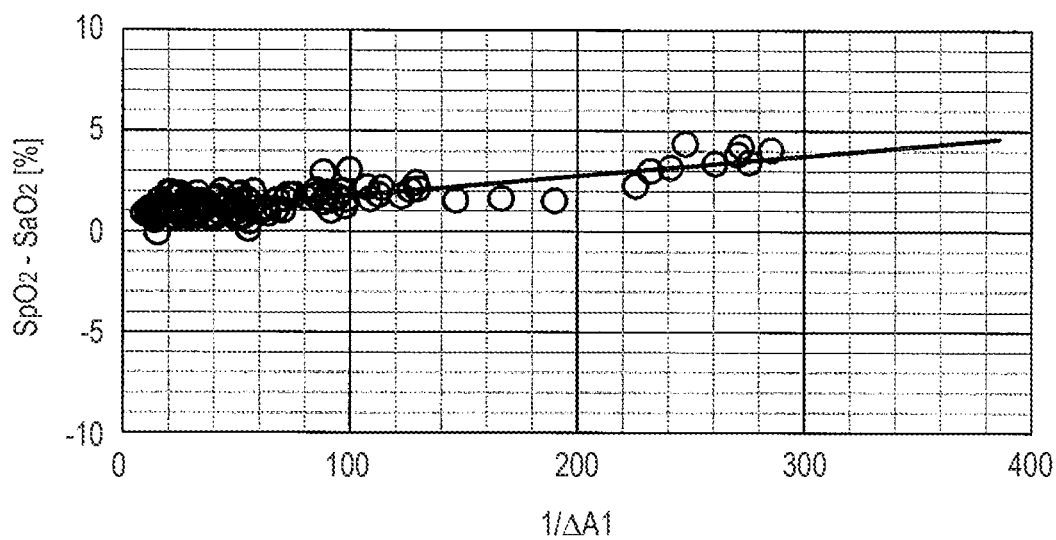
FIGS. 4(A) and 4(B) are views illustrating the operation of the pulse oximeter of FIG. 3.
Figure 4:
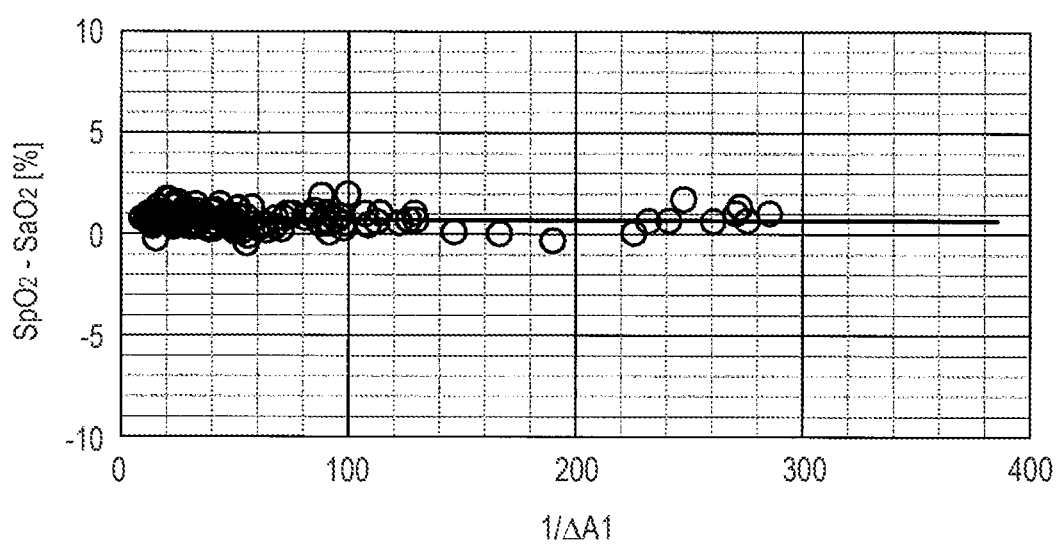

FIG. 4(A) illustrates relationships of the inverse of the light attenuation variation $\Delta A1$ of the first light beam in the case where the SpO2 is measured by using the three wavelengths, and the difference between the value of the SpO2 and that of the SaO2. The abscissa corresponds to the former, and the ordinate corresponds to the latter. The inventors have found that, also in the case where the three wavelengths are used, the inverse of the light attenuation variation $\Delta A1$ of the first light beam and the bias contained in the value of the acquired SpO2 are in proportional relationships.

The SpO2 is also a function of a light attenuation variation ratio $\Phi 31$ ($=\Delta A3/\Delta A1$) which is a ratio of the light attenuation variation $\Delta A3$ of the third light beam to the light attenuation variation $\Delta A1$ of the first light beam. From Expression (4), therefore, the following expression is obtained:

$$SaO2 \propto \Phi 21 + (k1/\Delta A1), \Phi 31 + (k2/\Delta A1) \quad (8)$$

$$\propto (\Delta A2/\Delta A1) + (k1/\Delta A1), (\Delta A3/\Delta A1) + (k2/\Delta A1)$$

$$\propto (\Delta A2 + k1)/\Delta A1, (\Delta A3 + k2)/\Delta A1$$

Namely, it is seen that the value of the SpO2 acquired by the pulse oximeter can approach that of the SaO2 by adding the first offset k1 which is obtained from the relationships shown in FIG. 4(A), to the light attenuation variation $\Delta A2$ of the second light beam, and further adding a second offset k2 to the light attenuation variation $\Delta A3$ of the third light beam.

The third variation acquirer 33 is configured so as to acquire a third variation $\Delta 3$ corresponding to the light attenuation variation $\Delta A3$ of the third light beam. The third variation $\Delta 3$ is set as the following expression based on the above-described finding:

$$\Delta 3 = \Delta A3 + k2 \quad (9)$$

In the expression, k2 is regarded as the second offset based on the inverse of the light attenuation variation $\Delta A1$ of the first light beam. That is, the third variation $\Delta 3$ contains the second offset k2.

The pulse oximeter 1A can include a concentration calculator 40A. The concentration calculator 40A is configured so as to calculate the SpO2 of the subject 2 based on the first variation $\Delta 1$ acquired by the first variation acquirer 31, the second variation $\Delta 2$ acquired by the second variation acquirer 32, and the third variation $\Delta 3$ acquired by the third variation acquirer 33. Specifically, the concentration calculator is configured so as to perform the process described below.

The light attenuation variations $\Delta A1$, $\Delta A2$, and $\Delta A3$ of the first, second, and third light beams are expressed by the following expressions:

$$\Delta A1 = \Delta Ab1 + \Delta At1 = Eb1Hb\Delta Db + \Sigma t1 \Delta Dt \quad (10)$$

$$\Delta A2 = \Delta Ab2 + \Delta At2 = Eb2Hb\Delta Db + \Sigma t2 \Delta Dt \quad (11)$$

$$\Delta A3 = \Delta Ab3 + \Delta At3 = Eb3Hb\Delta Db + \Sigma t3 \Delta Dt \quad (12)$$

where E is the extinction coefficient (dl $g^{-1}$ $cm^{-1}$), Hb is the hemoglobin concentration of blood (g $dl^{-1}$), $\Sigma$ indicates the light attenuation rate ($cm^{-1}$), and $\Delta D$ indicates the thickness change (cm) due to the blood pulsation. The suffix "b" means blood, the suffix "t" means the tissue except blood, the suffix "1" means the first light beam, the suffix "2" means the second light beam, and the suffix "3" means the third light beam.

Expressions (10) to (12) can be deformed in the following manner:

$$\Delta A1 = Eb1hb\Delta Db + \Sigma t1\Delta Dt \quad (13)$$
$$= [Eb1 + (\Sigma t1\Delta Dt)/(Hb\Delta Db)](Hb\Delta Db)$$
$$= (Eb1 + Ex1)(Hb\Delta Db)$$

$$\Delta A2 = Eb2Hb\Delta Db + \Sigma t2\Delta Dt \quad (14)$$
$$= [Eb2 + (\Sigma t2\Delta Dt)/(Hb\Delta Db)](Hb\Delta Db)$$
$$= (Eb2 + Ex2)(Hb\Delta Db)$$

$$\Delta A3 = Eb3Hb\Delta Db + \Sigma t3\Delta Dt \quad (15)$$
$$= [Eb3 + (\Sigma t3\Delta Dt)/(Hb\Delta Db)](Hb\Delta Db)$$
$$(Eb3 + Ex3)(Hb\Delta Db)$$

where Ex indicates a variable which is replaced with $[(\Sigma t\Delta Dt)/(Hb\Delta Db)]$, the suffix "1" means the first light beam, the suffix "2" means the second light beam, and the suffix "3" means the third light beam.

Expressions (13) to (15) can be deformed in the following manner:

$$Eb1+Ex1-\Delta A1/(Hb\Delta Db)=0 \qquad (16)$$

$$Eb2+Ex2-\Delta A2/(Hb\Delta Db)=0 \qquad (17)$$

$$Eb3+Ex3-\Delta A3/(Hb\Delta Db)=0 \qquad (18)$$

With respect to Expressions (16) to (18), the blood extinction coefficient Eb2 of the second light beam, and the blood extinction coefficient Eb3 of the third light beam can be approximated by the blood extinction coefficient Eb1 of the first light beam in the following manner:

$$Eb2=a2Eb1+b2 \qquad (19)$$

$$Eb3=a3Eb1+b3 \qquad (20)$$

where a and b are constants, the suffix "1" means the first light beam, the suffix "2" means the second light beam, and the suffix "3" means the third light beam.

With respect to Expressions (16) to (18), Ex2 of the second light beam and Ex3 of the third light beam can be approximated to by Ex1 of the first light beam in the following manner:

$$Ex2=\alpha 2Ex1+\beta 2 \qquad (21)$$

$$Ex3=\alpha 3Ex1+\beta 3 \qquad (22)$$

where $\alpha$ and $\beta$ are constants, the suffix "1" means the first light beam, the suffix "2" means the second light beam, and the suffix "3" means the third light beam.

Expressions (16) to (18) are rewritten by using Expressions (19) to (22), and the following expressions are obtained:

$$Eb1+Ex1-\Delta A1/(Hb\Delta Db)=0 \qquad (23)$$

$$(a2Eb1+b2)+(\alpha 2Ex1+\beta 2)-\Delta A2/(Hb\Delta Db)=0 \ a2Eb1+\alpha 2Ex1-\Delta A2/(Hb\Delta Db)=-b2-\beta 2 \qquad (24)$$

$$(a3Eb1+b3)+(\alpha 3Ex1+\beta 3)-\Delta A3/(Hb\Delta Db)=0 \ a3Eb1+\alpha 3Ex1-\Delta A3/(Hb\Delta Db)=-b3-\beta 3 \qquad (25)$$

When the following matrix expression is calculated, therefore, the blood extinction coefficient Eb1 of the first light beam is obtained:

$$\begin{pmatrix} 1 & 1 & -\Delta A1 \\ a2 & \alpha 2 & -\Delta A2 \\ a3 & \alpha 3 & -\Delta A3 \end{pmatrix} \begin{pmatrix} Eb1 \\ Ex1 \\ \frac{1}{Hb\Delta b} \end{pmatrix} = \begin{pmatrix} 0 \\ -b2-\beta 2 \\ -b3-\beta 3 \end{pmatrix} \qquad (26)$$

When the SpO2 which is expressed in a percentage notification is expressed as S which is expressed in a decimal notification, the blood extinction coefficient Eb1 is expressed by the following expression:

$$Eb1=Eo1S+Er1(1-S) \qquad (27)$$

where Eo is the extinction coefficient of oxyhemoglobin, Er is the extinction coefficient of deoxyhemoglobin, and the suffix "1" means the first light beam.

Here, it is seen that the value of SpO2 acquired by the pulse oximeter can approach that of the SaO2 by adding the first offset k1 to the light attenuation variation $\Delta A2$ of the second light beam, and adding the second offset k2 to the light attenuation variation $\Delta A3$ of the third light beam.

$$\begin{pmatrix} 1 & 1 & -\Delta A1 \\ a2 & \alpha 2 & -(\Delta A2+k1) \\ a3 & \alpha 3 & -(\Delta A3+k2) \end{pmatrix} \begin{pmatrix} Eb1 \\ Ex1 \\ \frac{1}{Hb\Delta b} \end{pmatrix} = \begin{pmatrix} 0 \\ -b2-\beta 2 \\ -b3-\beta 3 \end{pmatrix} \qquad (28)$$

Expression (28) is rewritten by using Expressions (6) and (9), and the following expression is obtained:

$$\begin{pmatrix} 1 & 1 & -\Delta 1 \\ a2 & \alpha 2 & -\Delta 2 \\ a3 & \alpha 3 & -\Delta 3 \end{pmatrix} \begin{pmatrix} Eb1 \\ Ex1 \\ \frac{1}{Hb\Delta b} \end{pmatrix} = \begin{pmatrix} 0 \\ -b2-\beta 2 \\ -b3-\beta 3 \end{pmatrix} \qquad (29)$$

Therefore, it is seen that the concentration calculator 40A is configured so as to calculate the SpO2 based on the first variation $\Delta 1$ acquired by the first variation acquirer 31, the second variation $\Delta 2$ acquired by the second variation acquirer 32, and the third variation $\Delta 3$ acquired by the third variation acquirer 33.

Similarly with FIG. 4(A), FIG. 4(B) illustrates the difference between the value of the SpO2 which is calculated by the pulse oximeter 1A including the concentration calculator 40A, and that of the SaO2. It is seen that the bias in a region where the pulse wave amplitude is low (region where the inverse of the light attenuation variation $\Delta A1$ of the first light beam is large) is greatly reduced as compared with the example in which the first offset k1 and the second offset k2 are not used. According to the configuration, therefore, it is possible to largely improve the accuracy of the SpO2 which is non-invasively calculated.

The values of the first offset k1 and the second offset k2 may be adequately determined. In the embodiment, the values of the first offset k1 and the second offset k2 are previously statistically determined based on a plurality of difference values between the SpO2 and the SaO2 which are acquired from a plurality of subjects. Specifically, a statistical process such as the least squares method is applied to a plurality of measurement results such as shown in FIG. 4(A), and the first offset k1 and second offset k2 by which the difference between the SpO2 and the SaO2 can be reduced are determined.

According to the configuration, the second variation acquirer 32 operates based on the first offset k1 which is a constant that is statistically determined, and the third variation acquirer 33 operates based on the second offset k2 which is a constant that is statistically determined. Therefore, the reliabilities of the first offset k1 and the second offset k2 can be improved, and furthermore the processing loads of the second variation acquirer 32 and the third variation acquirer 33 can be reduced. Consequently, the accuracy of the SpO2 which is non-invasively calculated can be easily and remarkably improved.

In the embodiment, an infrared light beam is used as the first light beam, and a red light beam is used as the second and third light beams. Alternatively, a red light beam may be used as the first light beam, a red light beam may be used as one of the second and third light beams, and an infrared light beam may be used as the other one of the second and third light beams. Alternatively, an infrared light beam may be used as two of the first, second, and third light beams, and a red light beam may be used as the remaining one of the light beams.

The embodiment is configured so that the common light detector 20 detects the first light beam emitted from the first light emitter 11, the second light beam emitted from the second light emitter 12, and the third light beam emitted from the third light emitter 13. Alternatively, a configuration may be employed where at least one of the light detector for detecting the first light beam, that for detecting the second light beam, and that for detecting the third light beam is independently arranged.

The red light beam and the infrared light beam are a combination in which ratios of the blood light absorbances are varied depending on the oxygen saturation, and therefore particularly the accuracy of the calculation of the SpO2 can be improved.

The above-described embodiments are mere examples for facilitating understanding of the invention. The configurations of the embodiments may be adequately changed or improved without departing from the spirit of the invention. It is obvious that equivalents are included within the technical scope of the invention.

In the above-described embodiments, a pulse oximeter for calculating the SpO2 has been exemplified. However, the presently disclosed subject matter can be applied also to other kinds of pulse photometers which measure the concentration of another blood light absorber. Examples of another blood light abosrober are carboxyhemoglobin, methhemoglobin, and a dye injected into blood vessels. In this case, the wavelengths of the light beams are selected so that combinations can be produced in which ratios of the blood light absorbances are substantially different from each other depending on the target blood light absorber concentration.

A configuration may be employed where four or more light beams at four or more wavelengths are used for identifying the blood light absorber concentration. For example, four wavelengths $\lambda 1$, $\lambda 2$, $\lambda 3$, and $\lambda 4$ may be selected as follows:

$\lambda 1$=630 nm, $\lambda 2$=660 nm, $\lambda 3$=700 nm, $\lambda 4$=880 nm; or
$\lambda 1$=660 nm, $\lambda 2$=700 nm, $\lambda 3$=880 nm, $\lambda 4$=940 nm.

In the above-described embodiments, the functions of the first variation acquirer 31, the second variation acquirer 32, the third variation acquirer 33, and the concentration calculator 40 (40A) are realized from software executed by a cooperation of a processor and memory which are communicable connected to each other. Examples of the processor are a CPU and an MPU. Examples of the memory are a RAM and a ROM. However, at least one of the functions of the first variation acquirer 31, the second variation acquirer 32, the third variation acquirer 33, and the concentration calculator 40 (40A) may be realized by hardware such as circuit devices, or a combination of hardware and software.

What is claimed is:

1. A pulse photometer comprising:
a first light emitter which is configured to emit a first light beam having a first wavelength;
a second light emitter which is configured to emit a second light beam having a second wavelength;
a light detector which is configured to output a first intensity signal in accordance with an intensity of the first light beam that is transmitted through or reflected from a body of a subject, and a second intensity signal in accordance with an intensity of the second light beam that is transmitted through or reflected from the body of the subject; and
at least one processor and memory configured to:
acquire a first variation based on the first intensity signal, wherein the first variation corresponds to a light attenuation variation of the first light beam resulting from pulsation of blood in the subject;
acquire a second variation based on the second intensity signal, wherein the second variation corresponds to a light attenuation variation of the second light beam adjusted by a first offset, the light attenuation variation of the second beam resulting from the pulsation of the blood in the subject; and
calculate a blood light absorber concentration, based on the first variation and the second variation,
wherein the first offset is based on an inverse of the light attenuation variation of the first light beam.

2. The pulse photometer according to claim 1, wherein the first offset is a constant that is previously statistically determined based on a plurality of blood light absorber concentrations acquired from a plurality of subjects.

3. The pulse photometer according to claim 1, wherein one of the first light beam and the second light beam is a red light beam, and the other of the first light beam and the second light beam is an infrared light beam.

4. The pulse photometer according to claim 1, further comprising:
a third light emitter,
wherein
the third light emitter is configured to emit a third light beam having a third wavelength,
the light detector is configured to output a third intensity signal in accordance with an intensity of the third light beam that is transmitted through or reflected from the body of the subject,
the at least one processor and memory are further configured to:
acquire a third variation based on the third intensity signal, wherein the third variation corresponds to a light attenuation variation of the third light beam adjusted by a second offset, the light attenuation variation of the third beam resulting from the pulsation of the blood in the subject, and
calculate the blood light absorber concentration, based on the first variation, the second variation, and the third variation, and
the second offset is based on an inverse of the light attenuation variation of the first light beam.

5. The pulse photometer according to claim 4, wherein the second offset is a constant that is previously statistically determined based on a plurality of blood light absorber concentrations acquired from a plurality of subjects.

6. The pulse photometer according to claim 4, wherein the first wavelength, the second wavelength, and the third wavelength are selected from 630 nm, 660 nm, 700 nm, 730 nm, 805 nm, 880 nm, and 940 nm.

7. The pulse photometer according to claim 1, wherein the second variation is identical to the light attenuation variation of the second light beam plus or minus the first offset, and wherein the first variation is identical to the light attenuation variation of the first light beam.

8. The pulse photometer according to claim 1, wherein:
the first variation is substantially equal to $\Delta 1=\ln[I1/(I1-\Delta I1)]$, where I1 is the first intensity signal,
the second variation is substantially equal to $\Delta 2=\ln[I2/(I2-\Delta I2)]+k1$, where I2 is the second intensity signal and k1 is the first offset, and k1 is based on the relationship 1/Δ1 and is statistically determined based on a plurality of difference values between transcutaneous arterial oxygen saturation and arterial oxygen saturation, such that the blood light absorber concentration corresponds to Δ2/Δ1.

9. The pulse photometer according to claim 1, wherein the first offset is statistically determined based on a plurality of difference values between transcutaneous arterial oxygen saturation and arterial oxygen saturation.

10. A pulse photometer comprising:
at least one processor and memory configured to:
acquire a first variation based on a first intensity signal, wherein the first variation corresponds to a light attenuation variation of a first light beam resulting from pulsation of blood in a subject, the first intensity signal corresponding to an intensity of the first light beam that is transmitted through or reflected from a body of the subject;
acquire a second variation based on a second intensity signal, wherein the second variation corresponds to a light attenuation variation of a second light beam adjusted by a first offset, the light attenuation variation of the second beam resulting from the pulsation of the blood in the subject, the second intensity signal corresponding to an intensity of the second light beam that is transmitted or reflected from the body of the subject; and
calculate a blood light absorber concentration, based on the first variation and the second variation,
wherein the first offset is based on an inverse of the light attenuation variation of the first light beam.

11. A method for calculating a blood light absorber concentration, the method comprising:
causing a pulse photometer to acquire a first variation based on a first intensity signal, wherein the first variation corresponds to a light attenuation variation of a first light beam resulting from pulsation of blood in a subject, the first intensity signal corresponding to an intensity of the first light beam that is transmitted through or reflected from a body of the subject;
causing the pulse photometer to acquire a second variation based on a second intensity signal, wherein the second variation corresponds to a light attenuation variation of a second light beam adjusted by a first offset, the light attenuation variation of the second beam resulting from the pulsation of the blood in the subject, the second intensity signal corresponding to an intensity of the second light beam that is transmitted through or reflected from the body of the subject; and
causing the pulse photometer to calculate the blood light absorber concentration, based on the first variation and the second variation,
wherein the first offset is based on an inverse of the light attenuation variation of the first light beam.

* * * * *